US008009295B2

(12) United States Patent
Cho

(10) Patent No.: US 8,009,295 B2
(45) Date of Patent: *Aug. 30, 2011

(54) CHEMICAL SENSING WITH NOISE PRE-COMPENSATION

(75) Inventor: Pak Shing Cho, Gaithersburg, MD (US)

(73) Assignee: CeLight, Inc., Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/711,476

(22) Filed: Feb. 24, 2010

(65) Prior Publication Data

US 2010/0290054 A1    Nov. 18, 2010

Related U.S. Application Data

(63) Continuation-in-part of application No. 12/635,848, filed on Dec. 11, 2009, and a continuation-in-part of application No. 12/361,664, filed on Jan. 29, 2009.

(51) Int. Cl.
 *G01B 9/02* (2006.01)
 *G01J 3/45* (2006.01)
(52) U.S. Cl. .................................................. 356/451
(58) Field of Classification Search .............. 356/128, 356/432, 451, 484, 517
See application file for complete search history.

(56) References Cited

U.S. PATENT DOCUMENTS

| | | | | |
|---|---|---|---|---|
| 6,709,857 | B2 * | 3/2004 | Bachur, Jr. | 435/288.7 |
| 7,203,251 | B2 * | 4/2007 | Kim et al. | 375/316 |
| 7,277,178 | B2 * | 10/2007 | Shpantzer et al. | 356/451 |
| 7,327,913 | B2 * | 2/2008 | Shpantzer et al. | 385/15 |
| 7,426,035 | B2 * | 9/2008 | Shpantzer | 356/451 |
| 7,483,600 | B2 * | 1/2009 | Achiam et al. | 385/14 |
| 7,502,118 | B2 * | 3/2009 | Shpantzer | 356/451 |
| 2009/0236528 | A1 * | 9/2009 | Shpantzer et al. | 250/339.07 |

* cited by examiner

*Primary Examiner* — Michael A Lyons
(74) *Attorney, Agent, or Firm* — Nadya Reingand

(57) ABSTRACT

This invention relates generally to the systems and methods for chemicals detection such as explosives and others, and more particularly to optical devices and the methods of their use based on sensing of gases and residue materials. This sensing includes detection of optical spectrum and relative concentration of the chemical followed by the chemical identification based on these data. The sensing is based on photothermal interferometry method modified by implementation of coherent optical detection using a balanced receiver, where the incoming optical signal is mixed with a local oscillator beam. An additional phase shift is embedded in the local oscillator beam for adaptively negating the background noise in the incoming optical signal thus improving the system performance.

20 Claims, 4 Drawing Sheets

CHEMICAL SENSING WITH NOISE PRE-COMPENSATION

CROSS-REFERENCE TO RELATED APPLICATIONS

This application is a continuation-in-part of U.S. Ser. No. 12/635,848 filed Dec. 11, 2009; and U.S. Ser. No. 12/361,664 filed Jan. 29, 2009, all of which applications are fully incorporated herein by reference.

FIELD OF INVENTION

This invention relates generally to systems and methods for chemical detection such as explosives and others, and more particularly to photothermal interferometric spectroscopy devices, and their methods of use, based on optical signal detection.

The present invention relates to the area of counter terrorism. Specifically, the present invention pertains to detection and identification of dangerous and hazardous trace chemical in vapor, liquid, or solid state from a safe standoff distance. The chemical include but not limited to trace explosive residues or vapor from, for example, person-borne and vehicle-borne improvised explosive devices, chemical warfare agents, hazardous chemicals, and chemical pollutants.

BACKGROUND OF THE INVENTION

The principles of photothermal spectroscopy are generally described in a publication by Stephen E. Bialkowski entitled "Photothermal Spectroscopy Methods for Chemical Analysis", John Wiley & Sons, Inc., 1996, the entire content of which is incorporated by reference herein. Photothermal spectroscopy method provides sensitive measurements of optical absorption in homogeneous and inhomogenous media.

McLean et al. (E. A. McLean et al. American Journal Applied Physics Letters, 13, p. 369 (1968)) recognized that the optical absorption resulting in sample heating and subsequent changes in refractive index would cause a phase shift in light passing through the heated region. This phase shift can be detected by interferometric means.

Grabiner et al. (F. R. Grabiner et al. Chemical Physics Letters, 17, p. 189 (1972)) proposed to use two lasers for photothermal interferometric spectroscopy: pulsed infrared laser for the medium excitation and visible probe laser for the refractive index change measurement.

In the U.S. Pat. No. 6,709,857 a system and method for monitoring the concentration of a medium using photothermal spectroscopy is disclosed. The system and method each employs an energy emitting device, such as a laser or any other suitable type of light emitting device, which is adapted to emit a first energy signal toward a location in the container. The first energy signal has a wavelength that is substantially equal to a wavelength at which the medium absorbs the first energy signal so that absorption of the first energy signal changes a refractive index of a portion of the medium. The system and method each also employs a second energy emitting device, adapted to emit a second energy signal toward the portion of the medium while the refractive index of the portion is changed by the first energy signal, and a detector, adapted to detect a portion of the second energy signal that passes through the portion of the medium. The system and method each further employs a signal analyzer, adapted to analyze the detected portion of the second energy signal to determine an amount of a sample in the container based on a concentration of the medium in the container.

In standoff chemical sensing method using photothermal interferometric detection has been disclosed by the same inventive entity as the present invention in U.S. Pat. No. 7,426,035, which is fully incorporated herein by reference. The system includes a strobe unit and a probe unit. The strobe beam changes the refractive index of chemical under study, and the probe beam reads out the information about the refractive index change. The probe subsystem employs a phase-diversity scheme where a six-port optical 90° hybrid is used to combine the interrogation probe beam and the reference or local oscillator (LO) laser beams. Two sets of balanced photoreceivers are employed to obtain two quadrature-phase homodyne signals, namely, $I=A\cos(\phi_n+\phi_s)$ and $Q=A\sin(\phi_n+\phi_s)$ where A is a proportion constant which depends on the square root of the received probe laser power.

There is a need for reliable remote methods and systems for detecting the presence of chemicals in the field. There is a need to provide highly sensitive receivers to improve signal-to-noise ratio of the detected signal, which gives an opportunity to detect traces of chemicals remotely.

SUMMARY OF THE INVENTION

The system and method are disclosed for chemical sensing (such as explosives and others) by coherent detection of optical beam. The chemical can be in a form of a gas, or liquid or solid substance. The chemicals are at remote location from the detection system.

The interrogated chemical is illuminated by a strobe beam, which changes its refraction index. This change of the refractive index is read out by the optical scheme proposed in the present invention. A probe beam is directed towards the chemical, and a change of the probe beam phase caused by the change of the refractive index, is detected. The novelty of this invention is in use of coherent detection scheme, where the received beam is mixed with a local oscillator beam in a mixer followed by a pair of balanced detectors. The local oscillator beam adaptively adds a phase shift, which negates background phase noise in the incoming signal, thus improving the system performance. This additional phase shift is embedded into the local oscillator beam using a phase modulator driven by an error signal derived from the received signal beam. The detection system provides homodyne detection of the received optical beam.

The error signal may be formed using a microprocessor, which receives a digital output signal from the balanced photoreceiver and processes it to create the error signal leading to elimination of the background noise in the received signal. Alternatively amplification and filtering may be applied to the received signal to create the error signal.

Another object of the present invention is a method to provide information about a chemical at a remote location using a coherent detection scheme with a feedback loop controlling the phase of the local oscillator beam in order to compensate the background noise in the received optical signal. In the preferred embodiment the method uses pulsed optical beams.

DETAILED DESCRIPTION OF THE PREFERRED EMBODIMENT

Figure 1:
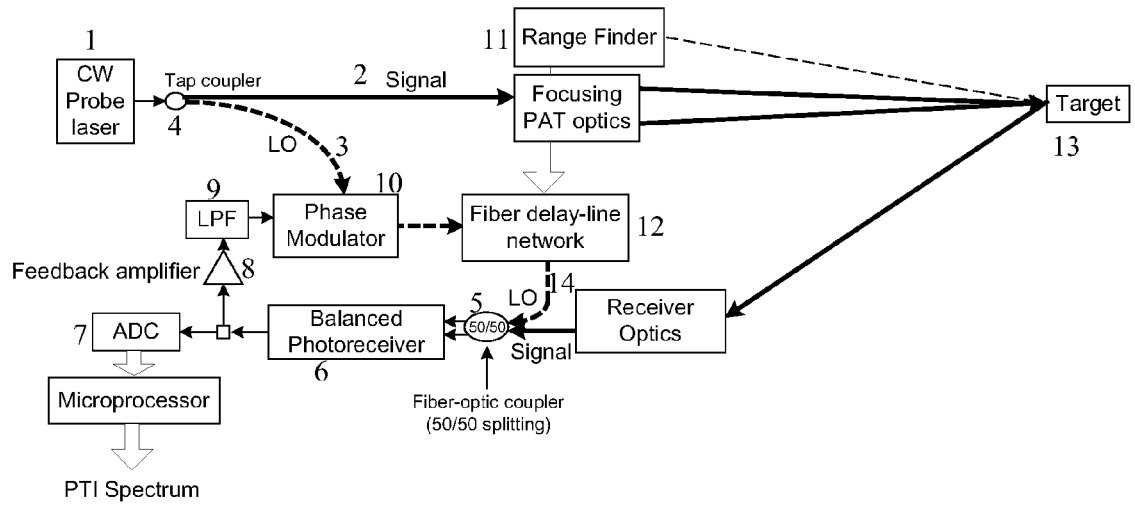
FIG. 1: First embodiment of the present invention with a single-pass configuration of the LO beam through the phase modulator and a fixed gain feedback amplifier. Heavy solid and dotted lines indicated the beam path of the signal and LO, respectively.

The present invention now will be described more fully hereinafter with reference to the accompanying drawings, in which the preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

In standoff chemical sensing method is based on interferometric signal detection as described in U.S. Pat. No. 7,426,035 by the same legal entity. The large background phase noise, $|\phi_n| \gg 1$, has a slow (milli-second) variation while the desired small photothermal phase shift transient, $|\phi_s| \ll 1$, occurs at a much faster time scale (micro-second). The absorption signature of the chemical compound is embedded in $\phi_s$, therefore recovering $\phi_s$ from the homodyne signals (I and Q) is essential for constructing the spectral signature of the chemical compound. The I and Q signals are simultaneously digitized by a pair of analog-to-digital converters (ADCs) and processed using noise-reduction algorithm to extract $\phi_s$ thereby recovering the absorbance information of the chemical compound of interest. This technique allows recovery of $\phi_s$ and the correct polarity via estimation of the large but slow-varying $\phi_n$ using noise estimation algorithm such as Kalman filtering. This is followed by coherent averaging of a large number of samples of $\phi_s$ in order to boost the signal-to-noise ratio (SNR). Consistent polarity of the $\phi_s$ samples is essential to achieve effective coherent averaging.

A closer look of the above phase-diversity detection scheme suggested in U.S. Pat. No. 7,426,035 reveals a serious drawback, namely, the dynamic range of the ADC is constrained by the large background phase noise $\phi_n$. In order for the Kalman filter to accurately estimate the phase noise, the slow but large $\phi_n$ must be captured and digitized by the ADC. Since $\phi_n$ is essentially not bounded the homodyned signals vary between $\pm A$ which means the input range, R, of the ADC must not be smaller than A, implying R>A. Otherwise, the homodyned signals will be clipped by the ADC thus risk losing information on both $\phi_n$ and $\phi_s$. The ADC resolution or smallest distinguishable input is $R/2^N$ for a N-bit digitizer which implies for the case of $\phi_n = 0$ the detectable $\phi_s$ is |A sin($\phi_s$)|≈A|$\phi_s$|≧R/$2^N$. Since R>A one can write $|\phi_s|>2^{-N}$ giving a lower bound of the detectable $\phi_s$. For example, a 14-bit digitizer gives $|\phi_s|>2^{-14}=61$ μrad. A high-pass electronic filter can be used to suppress the slow-varying $\phi_n$ before digitization to improve the dynamics range. However, important information on $\phi_n$ is also lost and is not available for the Kalman filter to accurately estimate the phase noise in order to recover the polarity of the $\phi_s$ samples for coherent averaging.

The present invention overcomes the above difficulty by using a closed-loop control configuration to actively suppress the background phase noise $\phi_n$ before digitization. An electro-optic phase modulator applied to the local oscillator (LO) path is driven by a control or error signal derived from a balanced detector output. An optical phase correction, $\phi_c$, produced by the phase modulator driven by the error signal reduces $\phi_n$ in a manner that minimizes the error signal which is proportional to the residual phase noise, $\phi_e = \phi_n - \phi_c$. The advantage is that the constraint on R>A is now relaxed since $\phi_n$ is reduced significantly before digitization. The maximum signal to be digitized is no longer A but reduces to approximately A|$\phi_e$| where |$\phi_e$|≪1 resulting into R>A|$\phi_e$|. The detectable $\phi_s$ now became $$A|\phi_s| \geq R/2^N \Rightarrow |\phi_s| \geq R/(2^N A) > (A|\phi_e|)/(2^N A)$$
$$\Rightarrow |\phi_s| > |\phi_e|/2^N.$$

For $|\phi_e|=0.1 \Rightarrow |\phi_s|>6.1$ μrad compared with $|\phi_s|>61$ μrad without noise pre-compensation. The lower bound of the detectable $\phi_s$ is reduced by a factor of $\phi_e$, in other words, the detection sensitivity is increased accordingly. Furthermore, Kalman filter can still be applied to the residual phase noise $\phi_e$ in post signal processing to achieve further noise reduction. As a result of the noise pre-compensation capability in the present invention only one homodyne signal, I or Q, is required. This is the case since the homodyne signals with noise suppression are given by $$I = A \cos(\phi_e + \phi_s) \approx 1 \text{ and } Q = A \sin(\phi_e + \phi_s) \approx A(\phi_e + \phi_s),$$

where $|\phi_e| \ll 1$ and $|\phi_s| \ll 1$.

Therefore, only one of the homodyne signals contains $\phi_s$. As a result, the optical hybrid can be replaced by a single directional coupler such as a two-by-two fiber-optic coupler.

The present invention use an architecture that employs a single passive fiber-optic coupler for optical mixing using only one set of balanced photoreceivers. This configuration not only achieved the phase noise suppression effect described above it also increases the signal strength by at least a factor of two. In addition, the present invention has the following advantages. A fiber-optic coupler is a simple, passive, compact, low-cost, wide-band, and robust device compared with an optical hybrid suggested in U.S. Pat. No. 7,426,035. Second, only one set of balanced photoreceivers and only one single-channel ADC is required. The processing and memory power required is halved since only one signal channel needs to be processed. Reducing processing time also reduces interrogation time allows more samples to be taken giving further increase in SNR. The cost and complexity reduction as well as the enhanced detection performance of the probe subsystem in the standoff chemical sensing system using the present invention is significant.

Experimental Results

FIG. 1 shows an embodiment of the probe subsystem in the present invention. A beam from CW probe laser 1 is divided into two paths 2 and 3, indicated by the heavy solid and dotted lines, as signal and LO via a tap coupler 4. The two beams are eventually combined via a two-by-two fiber-optic coupler 5 with a 50/50 splitting ratio thus forming a Mach-Zehnder interferometer (MZI). The 50/50 coupler 5 outputs are connected to a balanced photoreceiver 6 where its output is divided into two paths with one applied directly to the ADC 7. The other signal is amplified using a feedback amplifier 8 followed by a low-pass filter (LPF) 9 producing an error signal that is applied to an electro-optic phase modulator 10. The feedback amplifier 8 has a high input impedance to minimize loading. In respond to the applied error signal, the phase modulator 10 produces a counter optical phase shift that adaptively negates the large but slow background phase noise $\phi_n$. The cancellation continues as long as the output signal amplitude from the balanced photoreceiver is high. This process eventually leads to a much smaller signal ≈A $\sin(\phi_s+\phi_e)$ where $\phi_e$, is the residual phase noise ($|\phi_s|\ll1$). The fast signal phase shift $\phi_s$ has spectral power in the much higher frequency range is not affected by the phase modulator since the LPF eliminates high frequency components in the error signal. As a result, the phase modulator does not respond to $\phi_s$, the integrity of $\phi_s$ is therefore preserved. The gain and output voltage of the feedback amplifier are selected according to the half-wave voltage of the phase modulator and also the characteristics of the phase noise. FIG. 1 also shows a range finder 11 and a fiber delay-line network 12 that functions to suppress phase noise due to the finite linewidth of the probe laser and the unequal path length of the MZI. The range finder measures the distance from the probe transmitter to the target 13. The distance information is relayed to a fiber delay-line network 12 which provides the correct time delay to the LO beam 14 ensuring that the arrival time of the signal and LO beam at the 50/50 coupler matches.

The use of a simple two-by-two 50/50 fiber-optic coupler to combine the received probe signal and the LO beam before balanced detection as shown in FIG. 1 provides at least a factor of two increase in signal strength compared with a six-port optical hybrid employed in U.S. Pat. No. 7,426,035. This can be seen by considering the output signal of the balanced photoreceiver. For the six-port optical hybrid, the output signal is: $S_{hyb}=k_{hyb}C_g\sqrt{P_L P_s}\sin(\phi_n+\phi_s)$, where $C_g$ is the conversion gain of the balanced detector, $P_L$ and $P_s$ are optical powers of the LO and received signal, and $k_{hyb}$ is the excess loss of the hybrid typically around −2.5 dB or 0.56. In the present invention using a single 50/50 coupler the output signal is: $S_c=2k_c C_g\sqrt{P_L P_s}\sin(\phi_n+\phi_s)$ where $k_c$ is the excess loss of the fiber coupler typically not worst than −0.1 dB or 0.977. The factor of two is because only one 50/50 split is encountered by the optical beams in the present invention in contrast to two serial 50/50 splits for the optical hybrid case. The ratio of the output signals for the two cases is therefore $$S_c/S_{hyb}=2k_c/k_{hyb}=2(0.977/0.56)=3.4756 \text{ or } 5.41dB.$$

A signal gain of 5.41 dB is obtained for the present invention. A similar increase in the shot-noise limited SNR is expected ($S_c^2/\sigma_c^2$: shot-noise power increases by 3.4756 while signal power increases by $3.4756^2$ giving a net increase by 3.4756). To recap, a signal gain of 5.41 dB is obtained in the present invention as a result of using a single 50/50 fiber coupler which has almost zero excess loss (typically not worst than −0.1 dB) compared with −2 to −3 dB excess loss for a typical six-port optical hybrid device.

Figure 2:
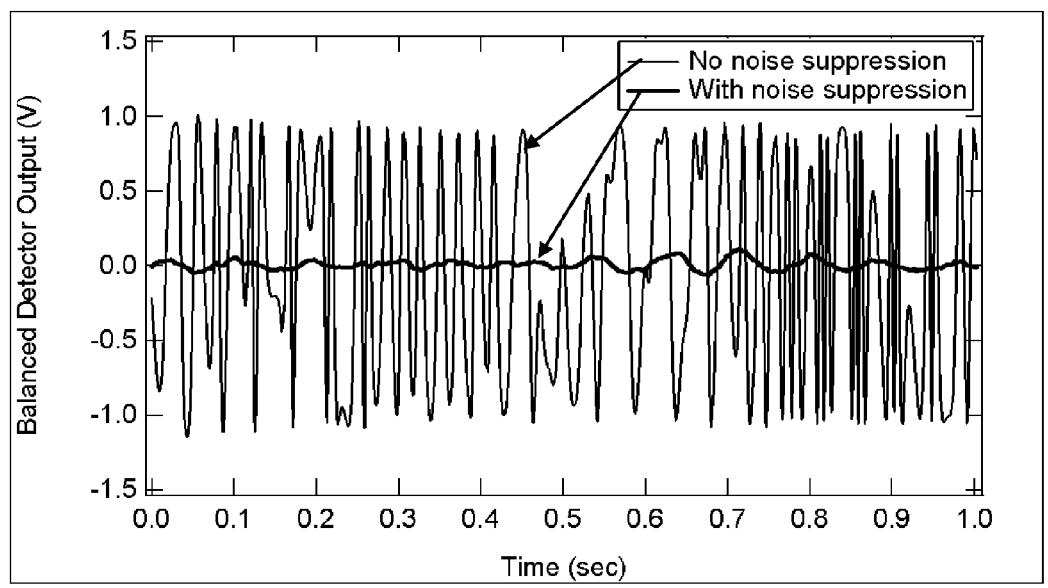
FIG. 2: Measured balanced detector output signal with and without noise suppression over 1 second.

The concept of the present invention was verified via experimentation using a test setup similar to that shown in FIG. 1. The output signal of the balanced photoreceiver was captured with (closed-loop) and without (opened-loop) noise suppression. FIG. 2 shows typical result where up to 1 second of the output signal is captured. Without noise suppression, large background phase noise due to the environment such as vibration can be seen (thin solid line). Significant reduction of the phase noise is obtained with the noise suppression activated (thick solid line). Statistics of the signal reveals that the standard deviation is reduced by a factor of 21, the peak-to-peak excursion reduced by a factor of 12, and the average value reduced by a factor of 10 using noise suppression. These are significant improvements showing the average residual phase noise is small $|\phi_e|_{max}<0.1$ rad.

Figure 3:
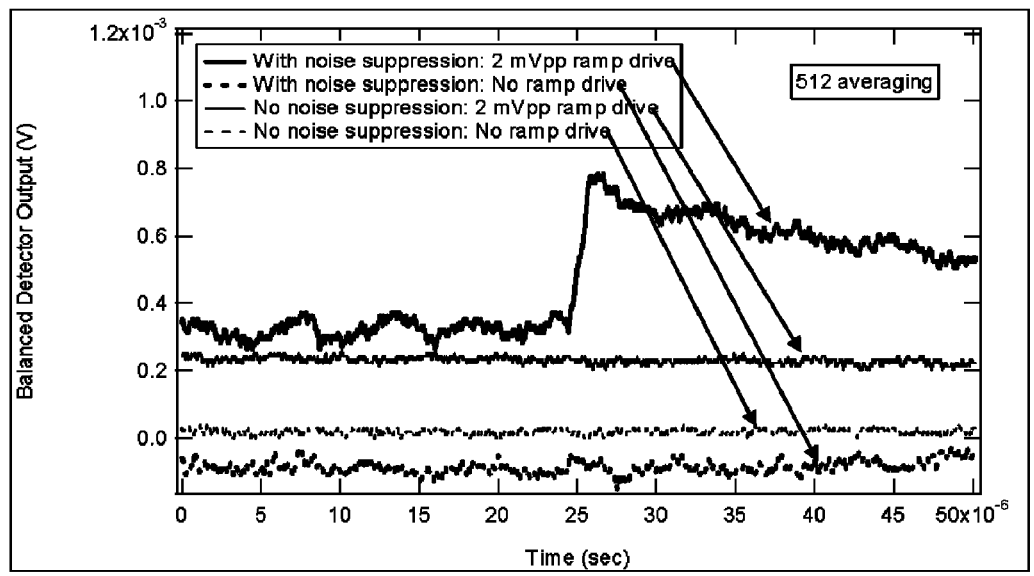
FIG. 3: Balanced detector output signal with a transient phase step that emulates photothermal phase shift. Signal averaging of 512 samples was applied. Time scale is 50 micro-second.

An experiment has also performed to verify that the noise suppression technique in the present invention preserves the fast photothermal transient phase shift. A fast transient phase shift was produced using a phase modulator driven by a fast (1 micro-second rise time) small amplitude ramp waveform to emulate the photothermal phase shift. FIG. 3 shows typical results with and without noise suppression within a time scale of 50 micro-second. With noise suppression, the transient step after 512 samples averaging can be clearly seen (heavy solid line). On the other hand, no transient phase step can be seen without noise suppression after 512 samples averaging (light solid line). This is because of the random polarity of the transient phase step in the samples as a result of the uncompensated large phase noise described earlier. Averaging of the transient step sample with random polarity cancels each other giving a net zero signal. With noise suppression, coherent averaging is achieved in which the signal polarity is constant from samples to samples giving a net increase in SNR. Baseline signals with no transient step applied are also shown with and without noise suppression (heavy and light dotted lines).

Figure 4:
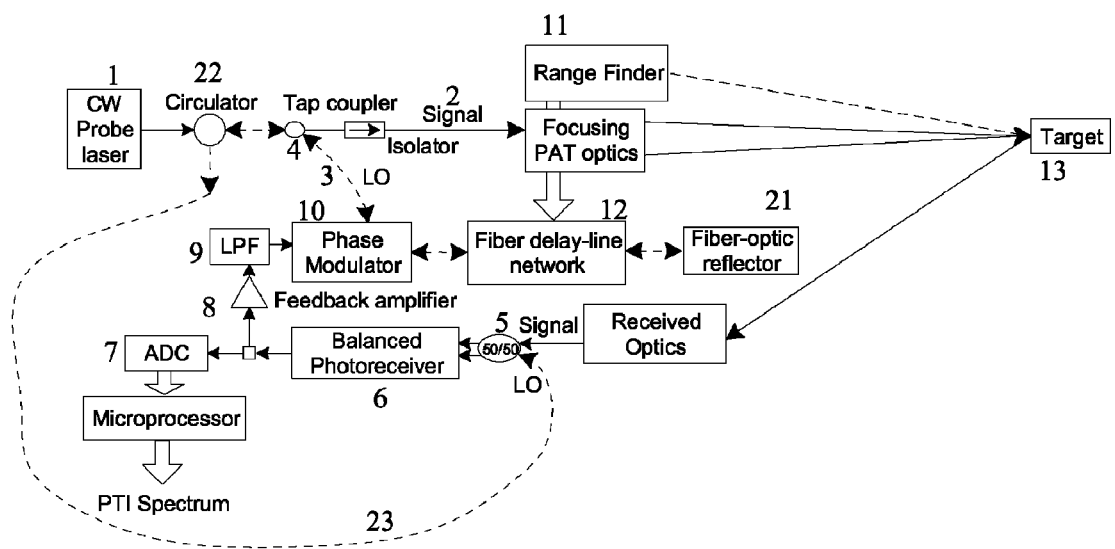
FIG. 4: Second embodiment of the present invention with a double-pass configuration and a fixed gain feedback amplifier.

A second embodiment of the present invention uses a double-pass configuration shown in FIG. 4. The LO beam path is directed to a fiber-optic reflector 21 which reflect the LO beam back retracing its path double passing through the same phase modulator 10. An advantage of this embodiment is the doubling amount of phase shift reducing the required applied drive voltage to the phase modulator. The returned LO beam 23 is diverted to the 50/50 coupler 5 via a circulator 22.

Figure 5:
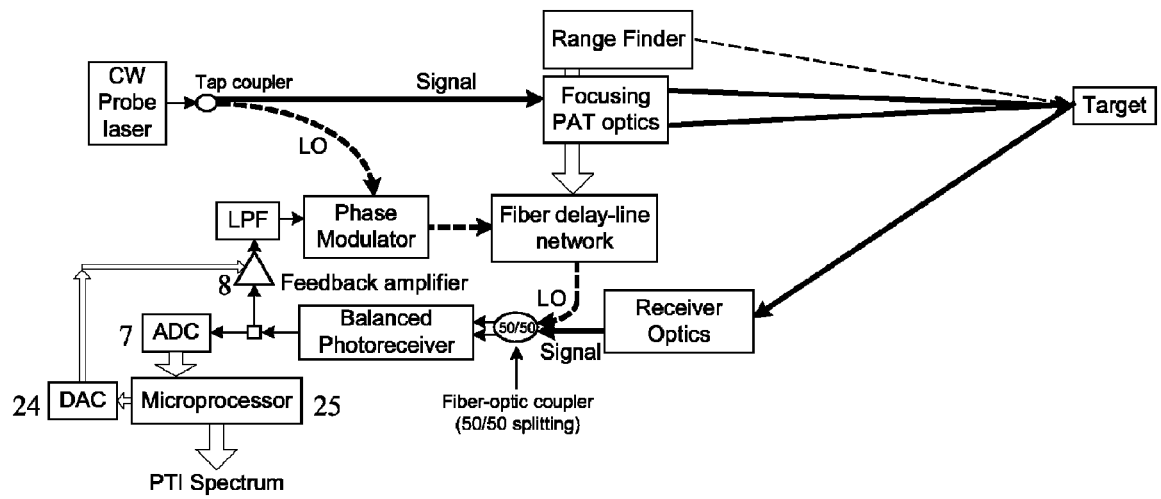
FIG. 5: Third embodiment of the present invention with a microprocessor-controlled feedback amplifier where its gain and/or output voltage can be adaptive adjusted in respond to the phase noise resulting into minimal amount of phase noise.

In the third embodiment of the present invention, the gain of the feedback amplifier can be controlled by a microprocessor in respond to change in the output signal as shown in FIG. 5. The gain and output voltage of the feedback amplifier 8 is adaptively adjusted to achieve an optimum value via a digital-to-analog converter (DAC) 24 connected to a microprocessor 25 in respond to the phase noise resulting into minimal amount of phase noise. As a result, fluctuation in the received signal power can be compensated without significant impact on the noise suppression performance. Furthermore, by adaptively adjusting the gain and therefore the output voltage of the feedback amplifier 8 in a manner that minimizes the error signal noise suppression can be enhanced with further reduction of the residual phase noise.

Figure 6:
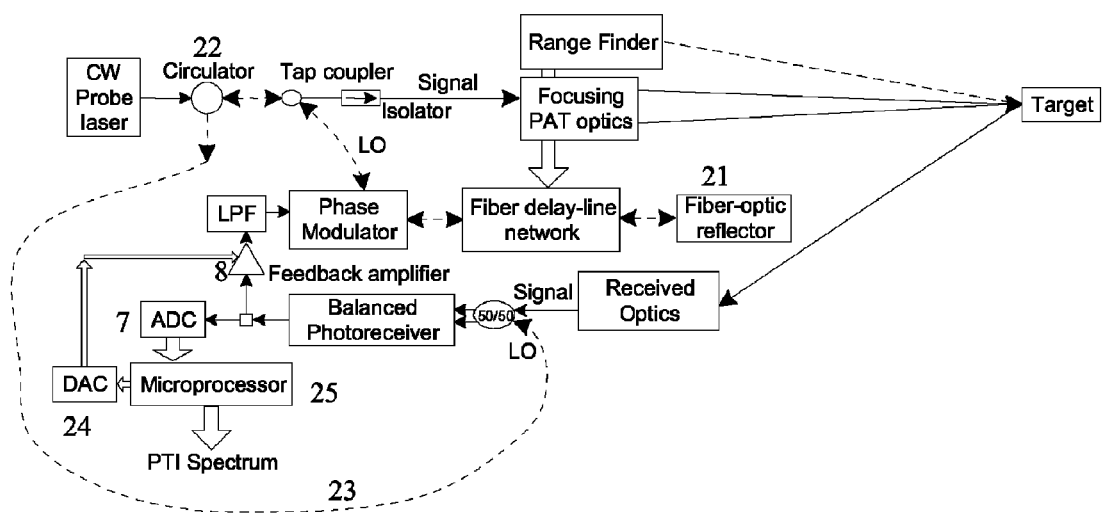
FIG. 6: Fourth embodiment of the present invention with a microprocessor-controlled feedback amplifier and a double-pass configuration for further performance enhancement.

In the fourth embodiment of the present invention, a microprocessor-controlled feedback amplifier (FIG. 5) combined with a double-pass configuration (FIG. 4) shown in FIG. 6 is disclosed. This provides further performance improvement in reducing the required error voltage applied to the phase modulator and the flexibility of adaptive gain control for performance enhancement.

Figure 7:
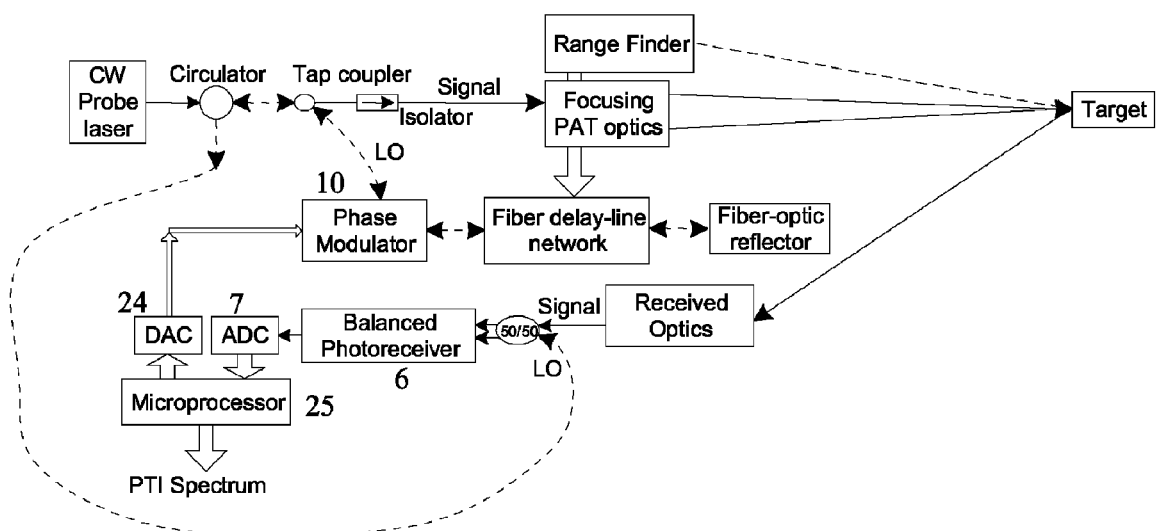
FIG. 7: Fifth embodiment of the present invention in a double-pass configuration with a microprocessor producing an error signal that is applied directly to the phase modulator.

In the fifth embodiment of the present invention shown in FIG. 7 an error signal produced by a microprocessor 25 is applied directly to the phase modulator 10. The balanced photoreceiver 6 output is directed to the ADC 7 connected to the microprocessor 25. The microprocessor performs digital signal processing and conditioning such as numerical filtering on the digitized signal. An error signal with proper magnitude and polarity is computed and outputted to the phase modulator via a DAC 24 in a manner such that the slow phase noise is minimized.

In summary, the present invention significantly improves the detection performance and reducing cost and complexity of a standoff trace chemical sensing system. Main advantages of the present invention are:

1. Increased detection sensitivity due to noise suppression before digitization giving $|\phi_s|>|\phi_e|/2^N$ with $|\phi_e|\ll 1$.
2. Increased detection sensitivity by at least a factor of two from increased signal strength as a result of a replacing a six-port optical hybrid with a single low-loss fiber coupler.
3. Background phase noise can be automatically suppressed without control algorithm.
4. Complex and costly optical hybrid replaced by a single simple, stable, robust, compact, and low-cost fiber-optic coupler.
5. Only one balanced photoreceiver is required.
6. Only one ADC channel is required.
7. Processing and memory usage in a microprocessor is reduced by a factor of two.
8. Reduced processing time give rise to a reduced interrogation time allows more samples to be acquired for coherent averaging which increases the SNR.

Although the invention has been described with reference to illustrative embodiments, this description should not be construed in a limiting sense. For example, a space-diversity receiver in conjunction with an adaptively controlled optical beam combiner as described in U.S. Pat. App. Pub. No. 20090185811 can be employed in the present invention to increase the SNR. Various modifications of the described embodiments, as well as other embodiments of the invention, which are apparent to persons skilled in the art to which the invention pertains, are deemed to lie within the principle and scope of the invention as expressed in the following claims.

What is claimed is:

1. A photo-thermal interferometric system that provides information about a chemical at a remote location, comprising:
   a first light source assembly that emits a first beam, the first beam having at least one wavelength that interacts with the chemical and changes a refractive index of the chemical;
   a second light source that produces a second beam, the second beam interacting with the chemical resulting in a third beam with a phase change that corresponds with the change of the refractive index of the chemical; and
   a detector system positioned remote from the chemical to receive at least a portion of the third beam, the detector system providing information on a phase change in the third beam relative to the second beam that is indicative of at least one of, absorption spectrum and concentration of the chemical;
   wherein the detector system includes one pair of balanced photodetectors.

2. The system of claim 1, wherein the detector system mixes the third beam with a local oscillator beam in a mixer.

3. The system of claim 2, wherein the local oscillator beam adaptively negates background phase noise of the third beam.

4. The system of claim 2, wherein the local oscillator beam carries a phase modulation, which compensates background phase noise of the third beam, the phase modulation being embedded into the local oscillator beam using a phase modulator, which is driven by an error signal, the error signal derived from the received third beam.

5. The system of claim 4, wherein the error signal is amplified in a feedback amplifier and filtered in a low pass filter.

6. The system of claim 5, wherein the feedback amplifier is controlled by a microprocessor; the microprocessor receiving a digital output signal from the detector system.

7. The system of claim 4, wherein the received signal is converted into a digital signal, processed in a microprocessor, and converted back into an analog signal serving as an error signal to control the phase modulator.

8. The system of claim 2, wherein the mixer is a directional coupler.

9. The system of claim 1, wherein chemical is in the form of a gas, liquid or solid.

10. The system of claim 1, wherein the remote location is selected from an explosive standoff location, outside of a blast range, inside a blast range, and at an entry point.

11. The system of claim 1, wherein the detection system provides homodyne detection of the third beam.

12. A method for determining information about a chemical at a remote location, comprising:
    directing a first beam to a remote location where a chemical is present, the first beam interacting with the chemical and changing a refractive index of the chemical;
    directing a second beam that interacts with the chemical, forming a third beam having a phase change relative to the second beam that corresponds with the change of a refractive index of the chemical;
    receiving at least a portion of the third beam at a detection system positioned remote from the chemical;
    measuring a phase shift of the third beam that is induced by the first beam and is indicative of at least one of absorption spectrum and concentration of the chemical, and
    wherein the detection scheme is operating in homodyne regime.

13. The method of claim 12, further comprising mixing the received portion of the third beam with a local oscillator beam in a balanced photoreceiver.

14. The method of claim 13, wherein the local oscillator beam has a phase modulation which negates a background phase noise of the third beam.

15. The method of claim 14, wherein the phase modulation is embedded into the local oscillator beam via a phase modulator driven by an error signal derived from the third beam.

16. The method of claim 15, wherein the error signal passes a low pass filter and a feedback amplifier.

17. The method of claim 15, wherein the error signal is generated in a microprocessor; the microprocessor receiving an output signal from the balanced photoreceiver.

18. The method of claim 12, wherein the second light beam is a pulsed beam.

19. The method of claim 12, wherein the chemical is in the form of a gas, liquid or solid.

20. The method of claim 12, wherein the chemical is selected from, an explosive device, a fuzing and one or more fuzing components.

* * * * *